United States Patent [19]

Niessner et al.

[11] Patent Number: 5,149,750

[45] Date of Patent: Sep. 22, 1992

[54] PREPARATION OF FINELY DIVIDED, GEL-LIKE, WATER-SWELLABLE COPOLYMERS

[75] Inventors: Manfred Niessner; Stefan Wickel, both of Ludwigshafen; Wilfried Heide, Freinsheim; Heinrich Hartmann, Limburgerhof, all of Fed. Rep. of Germany

[73] Assignee: BASF Aktiengesellschaft, Ludwigshafen, Fed. Rep. of Germany

[21] Appl. No.: 438,876

[22] Filed: Nov. 20, 1989

[30] Foreign Application Priority Data

Dec. 24, 1988 [DE] Fed. Rep. of Germany ....... 3843780

[51] Int. Cl.$^5$ ............... C08F 2/20; C08F 220/04; C08F 222/02
[52] U.S. Cl. ............................ 526/81; 526/207; 526/317.1; 526/318.2; 526/909; 526/930; 524/823
[58] Field of Search ............... 526/81, 78, 207, 317.1, 526/318.2, 909, 930; 524/823

[56] References Cited

U.S. PATENT DOCUMENTS

| | | | |
|---|---|---|---|
| 3,232,915 | 2/1966 | Bush et al. | 526/81 |
| 4,690,788 | 9/1987 | Yada et al. | 524/916 |
| 4,880,886 | 11/1989 | Kondo et al. | 526/81 |

*Primary Examiner*—Joseph L. Schofer
*Assistant Examiner*—Tom Weber
*Attorney, Agent, or Firm*—Oblon, Spivak, McClelland, Maier & Neustadt

[57] ABSTRACT

Finely divided, gel-like, water-swellable copolymers are prepared by copolymerizing (a) 100 parts by weight of water-soluble, monoethylenically unsaturated monomers, (b) from 0.01 to 5 parts by weight of monomers containing two or more ethylenically unsaturated double bonds and (c) from 0 to 20 parts by weight of water-insoluble, monoethylenically unsaturated monomers in 20–80% strength by weight aqueous solution in the presence of a polymerization initiator and from 0.1 to 10% by weight, based on the monomers used in the copolymerization, of a surfactant, by a process in which the monomers are copolymerized in the presence of initially from 0 to 50% by weight of the amount of surfactant to a conversion of not less than 60%, the remaining amount of surfactant is then added to the reaction mixture and the copolymerization is completed and the resulting gel particles dried.

5 Claims, No Drawings

PREPARATION OF FINELY DIVIDED, GEL-LIKE, WATER-SWELLABLE COPOLYMERS

U.S. Pat. No. 4,286,082 discloses a process for the preparation of water-absorbing polymers, in which alkali metal acrylates or mixtures of alkali metal acrylates and acrylic acid are polymerized together with a crosslinking monomer which contains from 2 to 4 ethylenically unsaturated double bonds in the molecule, in the presence of surfactants in not less than 25% strength by weight aqueous solution, and the resulting gel-like polymer is dried at elevated temperatures. The purpose of the surfactant is to improve the copolymerization of water-soluble monomers with the crosslinking agents. After the end of the polymerization, it is present on the surface and in the interior of the gel particles. The surfactant must be added to the reaction mixture before the polymerization. According to the patent, the addition of the surfactant after the end of the polymerization has an adverse effect on the quality of the product.

GB-A-2 146 343 discloses a process for the continuous preparation of water-absorbing crosslinked polymers in a twin-screw kneader, in which aqueous solutions of unneutralized or partially neutralized ethylenically unsaturated carboxylic acids are copolymerized together with a crosslinking agent in the presence of conventional polymerization initiators. This process gives polymer particles whose diameter generally does not exceed 3 cm and is usually from 0.05 to 1 cm. Since the particle size has a direct effect on the diffusion of water during the drying process, larger gel particles have to be dried for a longer time than smaller ones.

U.S. Pat. No. 4,769,427 discloses a process for the preparation of crosslinked finely divided, gel-like polymers in highly self-purging single-screw mixers. Monomer mixtures which contain from 0.01 to 5 parts by weight of a crosslinking agent per 100 parts by weight of, in each case, 50 to 100 mol % neutralized acrylic acid or methacrylic acid, acrylamide, methacrylamide or N-vinylpyrrolidone are subjected to polymerization in 20-65% strength by weight aqueous solution in the presence of initiators at from 45° to 95° C., and some of the water is removed from the reaction mixture under reduced pressure during the polymerization, so that a crumb-like gel having a solids content of from 30 to 70% by weight is discharged.

A similar process is disclosed in EP-A-0 238 050, in which process the copolymerization of, for example, methacrylic acid or acrylic acid, which may have been neutralized with alkali metal bases, and crosslinking agent is carried out as a multistage process in a batch mixing apparatus with constant thorough mixing in all stages, in the first stage of the polymerization the aqueous monomer solution being copolymerized at from 45° to 95° C. and under from 0.1 to 0.8 bar with partial removal of water by distillation, in the second stage the copolymerization being completed at from 100° to 170° C. and under not more than 8 bar and, after the pressure has been let down, in the third stage the water content of the resulting finely divided, crosslinked copolymer then being reduced to 0.5-10% by weight. In the two last-mentioned processes, a crumb-like polymer gel is formed, which can only be partially dried in the polymerization reactor. During the post-polymerization and during drying, the polymer gel is subjected to shearing to a greater or lesser extent, so that an undesirable change in the gel structure results.

It is an object of the present invention to provide a process for the preparation of finely divided, gel-like, water-swellable copolymers, which gives very finely divided gels whose structure is substantially retained during the post-polymerization and drying, which do not stick together and which are simple to handle and can be rapidly dried.

We have found that this object is achieved, according to the invention, by a process for the preparation of finely divided, gel-like, water-swellable copolymers by copolymerization of (a) water-soluble, monoethylenically unsaturated monomers,
(b) from 0.001 to 1 mol %, based on the monomers (a), of monomers containing two or more ethylenically unsaturated double bonds and
(c) from 0 to 20 mol %, based on the monomers (a), of water-insoluble, monoethylenically unsaturated monomers in 20-80% strength by weight aqueous solution in the presence of a polymerization initiator and from 0.1 to 10% by weight, based on the monomers used in the copolymerization, of a surfactant, at above 30° C. and with mixing, if the monomers are copolymerized in the presence of initially from 0 to 50% by weight of the amount of surfactant to a conversion of not less than 60% and the remaining amount of surfactant is then added to the reaction mixture and the copolymerization is completed.

If, as stated above, the surfactant is added to the reaction mixture after not less than 60% of the monomers have undergone copolymerization, the polymer gel surprisingly breaks up into small particles in the course of a few seconds. These finely divided gels are nontacky, can easily be stirred and can be dried under reduced pressure in the reactor. The presence of particularly finely divided gel-like copolymers after addition of the surfactant is evident from the fact that the particle size distribution of the gel-like copolymers can be determined by sieve analysis after treatment of the reaction mixture with methanol.

Water-soluble monoethylenically unsaturated monomers of group (a) are, for example, ethylenically unsaturated $C_3$–$C_6$-carboxylic acids and their amides and esters with amino alcohols of the formula

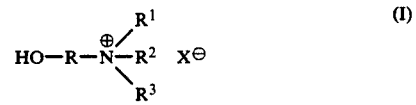

where R is $C_2$–$C_5$-alkylene and $R^1$, $R^2$ and $R^3$ are each H, $CH_3$, $C_2H_5$ or $C_3H_7$. These compounds are, for example, acrylic acid, methacrylic acid, crotonic acid, itaconic acid, maleic acid, fumaric acid, acrylamide, methacrylamide, crotonamide, dimethylaminoethyl acrylate, diethylaminoethyl acrylate, dimethylaminopropyl acrylate, dimethylaminobutyl acrylate, diethylaminoethyl methacrylate, dimethylaminoethyl methacrylate, dimethylaminopropyl acrylate, dimethylaminoneopentyl acrylate and dimethylaminoneopentyl methacrylate. The basic acrylates and methacrylates are used in the form of the salts with strong mineral acids, sulfonic acids or carboxylic acids or in quaternized form. The anion $X^{\ominus}$ of the compounds of the formula I is the acid radical of the mineral acids or the carboxylic acids or a methosulfate, ethosulfate or halide of a quaternizing agent.

Other water-soluble monomers of group (a) are N-vinylpyrrolidone, acrylamidopropanesulfonic acid, vinylphosphonic acid and/or alkali metal and ammonium salts of vinylsulfonic acid. The other acids can likewise be used either in unneutralized form or in partially or completely neutralized form in the polymerization. Further suitable water-soluble monomers of group (a) are diallylammonium compounds, such as dimethyldiallylammonium chloride, diethyldiallylammonium chloride and diallylpiperidinium bromide, N-vinylimidazolium compounds, such as salts or quaternization products of N-vinylimidazole and 1-vinyl-2-methylimidazole, and N-vinylimidazolines, such as N-vinylimidazoline, 1-vinyl-2-methylimidazoline, 1-vinyl-2-ethylimidazoline or 1-vinyl-2-n-propylimidazoline, which are likewise used in quaternized form or as salts in the polymerization. Preferred monomers of group (a) are acrylic acid, methacrylic acid, acrylamide and/or methacrylamide. These monomers may be copolymerized with one another in any ratio.

The polymerization of the monomers of group(a) is carried out in the presence of crosslinking agents (monomers of group (b)). The crosslinking agents contain two or more ethylenically unsaturated double bonds. Examples of suitable crosslinking agents are N,N'-methylenebisacrylamide, polyethylene glycol diacrylates and polyethylene glycol dimethacrylates, each of which is derived from a polyethylene glycol having a molecular weight of from 126 to 8,500, preferably from 400 to 2,000, trimethylolpropane triacrylate, trimethylolpropane trimethacrylate, ethylene glycol diacrylate, propylene glycol diacrylate, butanediol diacrylate, hexanediol diacrylate, hexanediol dimethacrylate, diacrylates and dimethacrylates of block copolymers of ethylene oxide and propylene oxide, polyhydric alcohols, such as glycerol or pentaerythritol, which are diesterified or triesterified with acrylic acid or methacrylic acid, triallylamine, tetraallylethylenediamine, divinylbenzene, diallyl phthalate, polyethylene glycol divinyl ethers of polyethylene glycols having a molecular weight of from 126 to 4,000, trimethylolpropane diallyl ether, butanediol divinyl ether, pentaerythritol triallyl ether and/or divinylethyleneurea. Water-soluble crosslinking agents, e.g. N,N'-methylenebisacrylamide, polyethylene glycol diacrylates, polyethylene glycol dimethacrylates, pentaerythritol triallyl ether and/or divinylurea, are preferably used. The monomers of group (b) are employed in the copolymerization in amounts of from 0.001 to 1, preferably from 0.005 to 0.5, mol %, based on the monomers (a).

If a change in the properties of the copolymers is desired, the copolymerization of the monomers of groups (a) and (b) may also be carried out in the presence of monomers of group (c). Examples of suitable monomers of group (c) are hydroxyethyl acrylate, hydroxypropyl acrylate, hydroxyethyl methacrylate, hydroxypropyl methacrylate, acrylonitrile and/or methacrylonitrile. Esters of acrylic acid or methacrylic acid with monohydric alcohols of 1 to 18 carbon atoms, e.g. methyl acrylate, ethyl acrylate, propyl acrylate, isopropyl acrylate, n-butyl acrylate, isobutyl acrylate, hexyl acrylate, 2-ethylhexyl acrylate, stearyl acrylate, the corresponding esters of methacrylic acid, diethyl fumarate, diethyl maleate, dimethyl maleate, dibutyl maleate, vinyl acetate and vinyl propionate, are also suitable. If the monomers of group (c) are used for modifying the water-soluble polymers, from 0.5 to 20, preferably from 2 to 10, mol %, based on the monomers (a), are used.

The polymerization may be carried out in the presence or absence of the conventional polymerization regulators. Examples of suitable polymerization regulators are thio compounds, such as thioglycollic acid, mercapto alcohols, e.g. 2-mercaptoethanol, mercaptopropanol and mercaptobutanol, dodecyl mercaptan, formic acid, ammonia and amines, e.g. ethanolamine, diethanolamine, triethanolamine, triethylamine, morpholine and piperidine.

The monomers (a), (b) and, where relevant, (c) are copolymerized with one another in 20–80, preferably 40–60, % strength by weight aqueous solution in the presence of polymerization initiators. All compounds which decompose into free radicals under the polymerization conditions may be used as polymerization initiators, for example peroxides, hydroperoxides, hydrogen peroxide, persulfates, azo compounds and the redox catalysts. Water-soluble catalysts are preferably used. In some cases, it is advantageous to use mixtures of different polymerization initiators, for example mixtures of hydrogen peroxide and sodium peroxydisulfate or potassium peroxydisulfate. Mixtures of hydrogen peroxide and sodium peroxydisulfate can be used in any ratio. Examples of suitable organic peroxides are acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, tert-butyl per-3,5,5-trimethylhexanoate and tert-amyl perneodecanoate. Other suitable polymerization initiators are azo initiators, e.g. 2,2'-azobis-(2-amidinopropane) dihydrochloride, 2,2'-azobis-(N,N'-dimethylene)-isobutyramidine dihydrochloride, 2-(carbamylazo)-isobutyronitrile and 4,4'-azobis-(4-cyanovaleric acid). The stated polymerization initiators are used in conventional amounts, for example in amounts of from 0.01 to 5, preferably from 0.1 to 2, mol %, based on the monomers to be polymerized.

The redox catalysts contain one or more of the abovementioned per compounds as oxidizing components and, as a reducing component, for example, ascorbic acid, glucose, sorbose, ammonium or alkali metal bisulfite, sulfite, thiosulfate, hyposulfite, pyrosulfite or sulfide, metal salts, such as iron(II) ions or silver ions or sodium hydroxymethyl sulfoxylate. Preferably used reducing components of the redox catalyst are ascorbic acid or sodium pyrosulfite. From $3.10^{-4}$ to 1 mol % of the reducing component of the redox catalyst system and from 0.01 to 5 mol % of the oxidizing component of the redox catalyst are used, the percentages being based on the amount of monomers used in the polymerization. Instead of the oxidizing component of the redox catalyst, it is also possible to use one or more water-soluble azo initiators.

For the preparation of the finely divided, gel-like, water-swellable copolymers, surfactants are required. All surfactants which have an HLB value of not less than 3 are suitable for this purpose (for the definition of the HLB value, see W. C. Griffin, J. Soc. Cosmetic Chem. 5 (1954), 249). Examples of suitable nonionic surfactants are the adducts of ethylene oxide, propylene oxide, or mixtures of ethylene oxide and propylene oxide, with alkylphenols, aliphatic alcohols, carboxylic acids and amines. For example, $C_8$–$C_{12}$-alkylphenols alkoxylated with ethylene oxide and/or propylene oxide are suitable. Commercial products of this type are, for example, octylphenols and nonylphenols which have each been reacted with from 4 to 20 moles of ethylene oxide per mole of phenol. Other nonionic surfactants are ethoxylated $C_{10}$–$C_{24}$-fatty alcohols or ethoxylated $C_{10}$–$C_{24}$-fatty acids and ethoxylated $C_{10}$–$C_{24}$-fatty amines or ethoxylated $C_{10}$–$C_{24}$-fatty amides. Polyhydric $C_3$–$C_6$-alcohols partially esterified with $C_{10}$–$C_{24}$-fatty acids are also suitable. These esters may additionally be reacted with from 2 to 20 moles of ethylene oxide. Examples of suitable fatty alcohols which are alkoxylated for the preparation of surfactants are palmityl alcohol, stearyl alcohol, myristyl alcohol, lauryl alcohol, oxo alcohols and unsaturated alcohols, such as oleyl alcohol. The fatty alcohols are ethoxylated or propoxylated, or reacted with ethylene oxide or propylene oxide, to a degree such that the reaction products are soluble in water. In general, 1 mole of the above-mentioned fatty alcohols is reacted with from 2 to 20 moles of ethylene oxide and, if required, with not more than 5 moles of propylene oxide to give surfactants which have an HLB value of more than 8.

$C_3$–$C_6$-alcohols which are partially esterified and may be ethoxylated are, for example, glycerol, sorbitol, mannitol and pentaerythritol. These polyhydric alcohols are partially esterified with $C_{10}$–$C_{24}$-fatty acids, for example oleic acid, stearic acid or palmitic acid. The degree of esterification with the fatty acids must be no higher than a level at which not less than one OH group of the polyhydric alcohol remains unesterified. Examples of suitable esterification products are sorbitan monooleate, sorbitan tristearate, mannitol monooleate, glycerol monooleate and glycerol dioleate. The stated fatty esters of polyhydric alcohols, which still contain one or more free OH groups, can be modified by also reacting them with ethylene oxide, propylene oxide or mixtures of ethylene oxide and propylene oxide. Preferably from 2 to 20 moles of the stated alkylene oxide are used per mole of fatty ester. The degree of ethoxylation is known to affect the HLB value of the nonionic surfactants. By suitable choice of the alkoxylating agents and of the amount of alkoxylating agent, it is possible to prepare surfactants having HLB values of from 3 to 20 in a technically simple manner.

Another group of suitable substances are homopolymers of ethylene oxide, block copolymers of ethylene oxide and alkylene oxides, preferably propylene oxide, and polyfunctional block copolymers which are formed, for example, by a sequential addition reaction of propylene oxide and ethylene oxide with diamines.

The nonionic surfactants can be used either alone or as mixture with one another. There are many possible variations here: for example, it is possible to use surfactants having different degrees of ethoxylation or alkoxylated phenols together with ethoxylated fatty alcohols or ethoxylated fatty alcohol derivatives. Other suitable surfactants are $C_8$–$C_{24}$-alkylsulfonates, which are preferably used in the form of the alkali metal salts, $C_8$–$C_{24}$-alkylsulfates, which are preferably used in the form of the alkali metal or trialkanolammonium salts, sulfosuccinic diesters, for example the sodium salt of di-(2-ethylhexyl) sulfosuccinate, sulfosuccinic half-esters, for example the disodium salt of castor oil acid/monoethanolamidosulfosuccinic acid or disodium fatty alcohol polyglycol ether sulfosuccinate, $C_8$–$C_{24}$-alkylarylsulfonic acids, for example the disodium salt of (dodecyldiphenyl ether)-disulfonic acid and the sulfuric half-esters of adducts of ethylene oxide with alkylphenols or fatty alcohols. Examples of suitable cationic surfactants are the adducts of alkylene oxides with fatty amines or salts of fatty amines, for example pentaoxyethyl-stearylammonium acetate or ethoxylated methyloleinamine methosulfate, and long-chain alkylbenzyldimethylammonium compounds, such as $C_{10}$–$C_{22}$-alkylbenzyldimethylammonium chloride. Other suitable cationic surfactants are the salts of fatty amines, for example coconut fatty ammonium acetate, quaternary fatty aminoesters, for example di-fatty acid-isopropylester-dimethylammonium methosulfate, and quaternary fatty aminoamides, for example N-undecylenoic acid-propylamido-N-trimethylammonium methosulfate. Amphoteric surfactants, for example those which carry one or more quaternary ammonium cations and one or more carboxylate or sulfonate anions in the same molecule, are also suitable. Commercial products of this type are, for example, dimethylcarboxymethyl-fatty acid-alkylamidoammonium betaines or 3-(3-fatty acid-amidopropyl)-dimethylammonium 2-hydroxypropane-sulfonates. The ionic surfactants can be used alone or as a mixture with one another, provided that the surfactant mixture does not lead to precipitation of the surfactants in water.

The surfactants are used in amounts of from 0.1 to 10, preferably from 0.5 to 5, % by weight, based on the monomers employed in the copolymerization.

The copolymerization is carried out with thorough mixing of the reactants. Since the viscosity of the reaction mixture increases considerably in the course of the polymerization, mixing apparatuses having a high degree of self-purging are required for the polymerization. The degree of self-purging of the suitable mixing apparatuses is greater than 80%. Suitable apparatuses which have a high self-purging effect are described in, for example, Chemie-Ingenieur-Technik 57 (1985), 1005. These apparatuses are preferably kneaders or suitably designed extruders. The mixing apparatuses may have one or more screws. The continuous preparation of crosslinked finely divided, gel-like polymers in such an apparatus having a high degree of self-purging is disclosed in, for example, U.S. Pat. No. 4,769,427. The copolymerization can be carried out continuously or batchwise.

According to the invention, the surfactant is fed into the reaction mixture in a special manner. The monomers (a) to (c) can first be copolymerized in the absence of surfactants to a conversion of not less than 60%, preferably 80%, and the total amount of surfactant then added, or an aqueous monomer solution which already contains surfactant is fed into the polymerization apparatus, the amount of surfactant being not more than 50% by weight of the total amount of surfactant used in the polymerization. The remaining amount of surfactant is not added to the reaction mixture until the monomers have undergone not less than 60%, preferably not less than 80%, conversion. For example, from 0 to 50, preferably from 0 to 20, % by weight of the amount of surfactant can be added to the aqueous monomer solution used in the copolymerization, and the remaining amount of surfactant, i.e. from 50 to 100, preferably from 80 to 100, % by weight, can then be added to the reaction mixture at a conversion of not less than 60%, preferably 80%. The surfactants are added to the reaction mixture after not less than 60% conversion of the monomers, preferably in the form of an aqueous solution which contains from 5 to 50% by weight of one or more surfactants. However, the surfactants can, if required, also be added in the undiluted state, for example in liquid form, as a melt or as a powder, to the reaction mixture being polymerized. The addition of the surfactant solution or of the surfactant after not less than 60% monomer conversion is effected in the course of a relatively short time, i.e. from 1 second to 5 minutes. In a continuous polymerization, the times correspond to the mean residence time in the region where the surfactant is metered in. As soon as the total amount of surfactant has been added to the polymer gel, it breaks up into small, non-tacky particles in the course of a few seconds under the polymerization conditions. As mentioned above, the viscosity of the reaction mixture increases considerably as the polymerization progresses. In a batchwise polymerization, this phenomenon is evident from the fact that the power consumption of the stirrer greatly increases. As soon as the surfactant has been added to the resulting polymer gel after not less than 60% monomer conversion, a sharp decrease in the power consumption of the stirrer is recorded. The power consumption decreases to a value measured before the beginning of the polymerization during stirring of the polymer solution having virtually the viscosity of water. Because of the fact that, after the addition of the remaining amount of surfactant, the gel breaks up into fine particles which do not agglomerate with one another and furthermore do not adhere to the walls and the stirrer shafts of the polymerization apparatus, the polymer gel is not damaged during post-polymerization and drying in the novel process. The polymerization can take place under atmospheric, reduced or superatmospheric pressure. In some cases, it may be advantageous to remove water from the system during the polymerization itself. By means of evaporative cooling, it is also possible to keep the polymerization temperature of the reaction mixture constant. The reaction mixture is preferably not cooled during the polymerization, so that the temperature increases, for example, from 40° C. to 100° C. After the addition of the remaining amount of surfactant to the reaction mixture, the copolymerization is completed, i.e. the monomers should as far as possible be completely polymerized, for example 95-99.5% polmerized. In some cases, it is also possible to achieve even higher conversions. The finely divided, gel-like copolymers are then dried. In production, drying is carried out, for example, in belt driers, fluidized-bed driers or paddle driers. The small particle diameter of the gel-like like copolymers not only leads to a reduction in the drying time compared with the drying times for the comparable copolymers prepared by conventional processes but also permits a reduction in the residual monomer content of the finely divided gels.

This procedure gives finely divided, gel-like, water-swellable copolymers which have a high water absorption and are therefore used as water-absorbing materials in hygiene articles, for example diapers, or as soil stabilizers. The water absorption and water retention of the gels obtainable by the novel process do not differ from those of the polymer gels which are obtainable in the absence of a surfactant and for whose preparation the total amount of surfactant was used before the polymerization.

However, the method of surfactant addition has an effect on the amount of soluble constituents in the polymer gels. If, as described in the prior art, the total amount of surfactant is added to the monomer solution, the polymer gels have substantially higher soluble fractions than the polymer gels which can be prepared by the novel process and where the monomer solution contains no surfactant or not more than 50% by weight of the required surfactant and where the total amount of surfactant or the residual amount of surfactant is added after a monomer conversion of not less than 60% by weight has been reached. A low content of soluble constituents in the polymer gel is an advantage in practice.

In the Examples which follow, percentages are by weight. The following surfactants were used:

Surfactant 1: Sodium salt of a $C_{14}$-alkylsulfonic acid

Surfactant 2: Sodium salt of di-(2-ethylhexyl) sulfosuccinate

Surfactant 3: Disodium salt of (dodecyldiphenyl ether)-disulfonic acid

Surfactant 4: Disodium salt of castor oil acid monoethanol amidosulfosuccinate

Surfactant 5: Sodium laurylsulfate

Surfactant 6: Sodium salt of the sulfuric half-ester of a reaction product of 25 moles of ethylene oxide with 1 mole of isooctylphenol Surfactant 7: Adduct of 8 moles of ethylene oxide with 1 mole of $C_9$-alkylphenol Surfactant 8: Adduct of 5 moles of ethylene oxide with 1 mole of a $C_{13}/C_{15}$-oxo alcohol Surfactant 9: Adduct of 50 moles of ethylene oxide with 1 mole of a $C_{16}/C_{18}$-fatty alcohol Surfactant 10: Adduct of 12 moles of ethylene oxide with 1 mole of castor oil Surfactant 11: Adduct of 7 moles of ethylene oxide with 1 mole of oleinamine methosulfate Surfactant 12: Dimethylcarboxymethyl-lauric acid-propylamidoammonium betaine Surfactant 13: $C_{12}/C_{14}$-alkylbenzyldimethylammoniun chloride Surfactant 14: Polyethyleneglycol having a molecular weight of 300

Surfactant 15: Sorbitan monooleate

EXAMPLES 1 TO 15

General Method of Preparation 26 ml of a 0.5% strength aqueous solution of N,N-methylenebisacrylamide and 3 g of a 1% strength aqueous solution of diethylenetriaminepentasodium acetate were added to 1,000 g of a 43% strength aqueous solution of 75 mol % of sodium acrylate and 25 mol % of acrylic acid. This monomer solution was introduced into a kneader whose wall temperature was 60° C. As soon as the temperature of the monomer solution had reached 40° C., first 4.3 g of sodium peroxydisulfate, dissolved in 25 ml of water, and then a solution of 0.13 g of sodium disulfite in 25 ml of water were added with constant thorough mixing. The beginning of polymerization was evident from the increase in the temperature of the reaction mixture. Table 1 shows the maximum temperatures reached by the reaction mixture and the calculated monomer conversions at which 1%, based on the monomers originally used in the polymerization, of a surfactant was then metered in, the said surfactant likewise being indicated in Table 1. The addition of the surfactant to the reaction mixture led within a few seconds to the breaking up of the originally cohesive polymer gel into small particles. At the same time, the power consumption of the stirrer, which had increased during the polymerization reaction, decreased to a value measured before the beginning of the polymerization during stirring of the monomer solution, which had virtually the viscosity of water. About 3-5 minutes after the addition of the surfactant solution, the pressure in the reactor was successively reduced, so that some of the water present distilled off. Under these conditions, the polymerization was completed, i.e. to a monomer conversion of about 99%.

In each Example, as 1.25 below 100 g of the polymer gel prepared in this manner were introduced into 1,000 ml of methanol and stirred therein for 30 minutes with a propeller stirrer at 300 rpm. The water-containing, methanol-moist gel was filtered off under suction and subjected to sieve analysis. The remaining untreated gel was dried in a drying oven under reduced pressure, milled and screened. The water absorptivity of the dry powder was determined. Table 1 shows the surfactants used in each of the Examples, the result of the sieve analyses, the amount of water distilled off during the post-polymerization and the absorptivity of the finely divided, gel-like, water-swellable copolymers. Determination of the absorptivity The absorptivity is determined by the teabag test. The liquid used is a 0.9% strength sodium chloride solution. A defined amount of gel-like, water-absorbing copolymer (1 g) is introduced into a teabag, which is then sealed. The dimensions of the teabag must be appropriately adapted to the amount of gel-like copolymer weighed in. The teabag is then immersed in the liquid for a certain time, allowed to drip off for 15 seconds and then reweighed. In order to calculate the absorptivity, it is necessary to carry out a blank test in which a teabag without gel-like, water-absorbing copolymer is immersed in the solution and the weight of the teabag is determined after the abovementioned drip-off time. The absorptivity is then obtained from the following relationship $$\text{Absorptivity} = \frac{\text{Weight of teabag with polymer gel} - \text{weight of teabag in blank test}}{\text{Weight of polymer gel taken}}$$

COMPARATIVE EXAMPLE 1

The abovementioned Examples were repeated, except that the copolymerization was now carried out in the absence of a surfactant. This gave a coarse crumb-like gel whose particle size increased steadily even after the maximum temperature had been reached. The agglomerated gel-like particles underwent pronounced kneading, compaction and shearing. This finding was evident from the constantly increasing power consumption of the stirrer. As soon as the pressure in the reactor was reduced and water distilled off, the power consumption of the stirrer increased to such an extent that the experiments had to be terminated after only a few ml of water had been distilled off. The polymer was obtained in the form of a dough-like, viscous, cohesive mass. It was impossible to discharge individual particles or to conduct a sieve analysis.

COMPARATIVE EXAMPLE 2

Example 4 was repeated, except that the surfactant used therein, likewise in an amount of 1%, based on the monomers used in the polymerization, was added to the aqueous monomer solution before the beginning of the polymerization. In this case, a coarse crumb-like tacky polymer gel was obtained whose polymer particles showed pronounced agglomeration when water was distilled off, with the result that the power consumption of the stirrer considerably increased. After 30 ml of water had been distilled off, the experiment had to be terminated; a sieve analysis of the resulting coarse-particle product and the absorptivity of the copolymer are shown in Table 1.

TABLE 1

| | $T^{1)}$ max. [°C.] | Surfactant | Surfactant addition after conversion of ... % | Sieve analysis | | | | | | Water distilled off [ml] | Absorptivity of the polymer gels [g/g] |
| --- | --- | --- | --- | --- | --- | --- | --- | --- | --- | --- | --- |
| | | | | >4 mm [%] | >3 mm [%] | >2 mm [%] | >1 mm [%] | <1 mm [%] | Sum <2 mm [%] | | |
| Example No. | | | | | | | | | | | |
| 1 | 69 | Surfactant 1 | 89 | 35.8 | 15.9 | 23.4 | 20.0 | 4.8 | 24.8 | 50 | 40 |
| 2 | 68 | Surfactant 2 | 92 | 25.6 | 13.9 | 25.8 | 28.7 | 6.0 | 34.7 | 250 | 40 |
| 3 | 68 | Surfactant 3 | 75 | 25.2 | 12.4 | 23.9 | 28.3 | 10.2 | 38.5 | 200 | 45 |
| 4 | 68 | Surfactant 4 | 96 | 16.0 | 13.2 | 22.5 | 35.4 | 12.9 | 48.3 | 150 | 40 |
| 5 | 68 | Surfactant 5 | 84 | 26.6 | 12.8 | 28.0 | 30.4 | 2.1 | 32.7 | 80 | 44 |
| 6 | 68 | Surfactant 6 | 80 | 24.2 | 15.1 | 30.1 | 25.5 | 5.2 | 30.7 | 50 | 40 |
| 7 | 70 | Surfactant 7 | 95 | 44.0 | 16.4 | 20.6 | 15.2 | 3.8 | 19.0 | 0 | 45 |
| 8 | 68 | Surfactant 8 | 87 | 30.6 | 15.0 | 23.5 | 25.3 | 5.7 | 31.0 | 50 | 40 |
| 9 | 68 | Surfactant 9 | 85 | 14.3 | 11.2 | 31.5 | 36.1 | 6.8 | 42.9 | 60 | 50 |
| 10 | 69 | Surfactant 10 | 90 | 21.1 | 15.1 | 31.6 | 28.4 | 3.9 | 32.3 | 60 | 38 |
| 11 | 73 | Surfactant 11 | 84 | 16.0 | 13.0 | 25.1 | 34.1 | 11.9 | 46.0 | 200 | 41 |
| 12 | 69 | Surfactant 12 | 93 | 18.0 | 11.4 | 23.9 | 36.4 | 11.3 | 47.7 | 200 | 39 |
| 13 | 69 | Surfactant 13 | 85 | 23.6 | 13.0 | 26.6 | 30.0 | 6.7 | 36.7 | 40 | 48 |
| 14 | 68 | Surfactant 14 | 96 | 47.5 | 11.4 | 19.2 | 17.9 | 3.9 | 21.8 | 20 | 48 |
| 15 | 76 | Surfactant 15 | 93 | 19.5 | 13.7 | 30.3 | 31.0 | 5.5 | 36.5 | 200 | 37 |
| Comparative Example | | | | | | | | | | | |
| 2 | 69 | Surfactant 4 | 93 | 59.4 | 11.2 | 14.0 | 12.0 | 3.3 | 15.3 | 30 | 42 |

[1)]Maximum temperature reached during the polymerization

EXAMPLES 16 TO 21

1.7 g of a polyethylene glycol diacrylate whose polyethylene glycol segment had a molecular weight of 300 and 3 g of a 1% strength aqueous solution of diethylenetriaminepentasodium acetate were added to 1,000 g of a 43% strength aqueous solution of 61 mol % of sodium acrylate and 39 mol % of acrylic acid. The aqueous monomer solution was introduced into a preheated kneader which had a wall temperature of 60° C. As soon as the temperature of the aqueous monomer solution in the kneader reached 40° C., first 1 g of potassium bution of the gel particles obtainable in this manner is shown in Table 2.

TABLE 2

| | $T_{max.}$ [°C.] | Surfactant | Surfactant addition after conversion of ... % | Sieve analysis | | | | | | Water distilled off [ml] |
|---|---|---|---|---|---|---|---|---|---|---|
| | | | | >4 mm [%] | >3 mm [%] | >2 mm [%] | >1 mm [%] | <1 mm [%] | Total <2 mm [%] | |
| Example | | | | | | | | | | |
| 16 | 87 | Surfactant 2 | 96 | 9.7 | 7.7 | 17.2 | 42.6 | 22.8 | 65.4 | 100 |
| 17 | 90 | Surfactant 3 | 75 | 2.4 | 4.0 | 17.2 | 58.6 | 17.9 | 76.5 | 250 |
| 18 | 93 | Surfactant 4 | 87 | 1.7 | 1.7 | 9.9 | 48.7 | 38.1 | 86.8 | 40 |
| 19 | 87 | Surfactant 9 | 89 | 2.0 | 3.0 | 12.7 | 57.0 | 25.4 | 82.4 | 50 |
| 20 | 90 | Surfactant 11 | 93 | 8.2 | 6.6 | 18.0 | 45.7 | 21.6 | 67.3 | 50 |
| 21 | 95 | Surfactant 12 | 93 | 1.0 | 1.6 | 12.1 | 58.6 | 26.8 | 85.4 | 100 |
| Comparative Example | | | | | | | | | | |
| 4 | 95 | Surfactant 9 | — | 41.2 | 3.9 | 10.8 | 25.8 | 18.3 | 44.1 | 30 | peroxydisulfate, dissolved in 25 ml of water, and then a solution of 0.08 g of sodium disulfite in 25 ml of water were added. The beginning of polymerization was evident from an increase in temperature. The temperature increased to the maximum values ($T_{max}$) indicated in Table 2. One minute after the maximum reaction temperature had been reached, the conversions were those shown in Table 2. 1% of the surfactant stated in Table 2 was then metered in over 5 seconds in each case. The initially coarse crumb-like gel was broken up into small particles within a few seconds after the addition of the surfactant. At the same time, the power consumption of the stirrer, which had increased during the polymerization reaction, decreased to about the value measured before the beginning of polymerization during stirring of the monomer solution, which had virtually the viscosity of water. About 3–5 minutes after the addition of the surfactant, the pressure in the reactor was reduced successively to 100 mbar, so that some of the water present distilled off, and the polymerization was completed. The amount of distillate is stated in Table 2. The conversion of the monomers was then 99%. As described in Examples 1 to 15, the particle size distributions of the polymer gels were then determined. The results are summarized in Table 2.

COMPARATIVE EXAMPLE 3

Examples 16 to 21 were repeated, except that the copolymerization was carried out in the absence of a surfactant. The polymer gel obtained in this procedure agglomerated during the subsequent reaction to give steadily growing particles which stuck together rapidly to give a cohesive mass after the internal pressure in the reactor was reduced. The polymer gel underwent continuous pronounced shearing, kneading and compacting. The power consumption of the stirrer increased rapidly and the stirrer finally came to a stop. The cohesive mass could be removed from the kneader only after mechanical comminution; a sieve analysis was therefore impossible.

COMPARATIVE EXAMPLE 4

Example 19 was repeated in such a way that the total amount of surfactant 9, likewise 1%, based on the monomers used in the copolymerization, was added to the aqueous monomer solution itself. The power consumption of the stirrer increased constantly even after the maximum temperature had been reached and particularly rapidly after reduction of the internal pressure in the reactor. The experiment was terminated after 30 ml of water had been distilled off. The particle size distri-

EXAMPLE 22

Example 4 was repeated with concentrations of crosslinking agents of
a) 0.03% by weight and
b) 0.10% by weight.
The soluble constituents of the polymer were then determined in each case. The following values were obtained:
a) 10% by weight and
b) 2.9% by weight.

COMPARATIVE EXAMPLE 5

Comparative Example 2 was repeated using concentrations of crosslinking agents of
a) 0.03% by weight and
b) 0.10% by weight.
The soluble constituents present in the polymer gel were then determined and were found to be
a) 13.7% by weight and
b) 6.1% by weight.
Comparison with the results of Example 22 shows that the copolymers prepared by the process of U.S. Pat. No. 4,286,082 have significantly higher soluble fractions than copolymer gels according to the invention.

We claim:

1. A process for the preparation of a finely divided, gel-like, water-swellable copolymer, which comprises copolymerizing
(a) water-soluble, monoethylenically unsaturated monomers,
(b) from 0.001 to 1 mol %, based on the monomers (a), of monomers containing two or more ethylenically unsaturated double bonds and
(c) from 0 to 20 mol %, based on the monomers (a), of water-insoluble, monoethylenically unsaturated monomers,
in 20–80% strength by weight aqueous solution in the presence of a polymerization initiator and from 0.1 to 10% by weight, based on the monomers used in the copolymerization, of a surfactant having an HLB value of not less than 3, the monomers being copolymerized in the presence of initially from 0 to 50% by weight of the amount of surfactant to a conversion of not less than 60% with thorough mixing, the remaining amount of surfactant then being added to the reaction mixture, the copolymerization being completed and the gel-like copolymer obtained in finely divided form then being dried.

2. A process as claimed in claim 1, wherein the monomers are copolymerized in the presence of initially from 0 to 50% by weight of the amount of surfactant to a conversion of not less than 80%.

3. A process as claimed in claim 1, wherein the monomers of group (a) are copolymerized with water-soluble monomers of group (b), initially in the absence of surfactants, to a conversion of not less than 80%, and the total amount of surfactant is then added.

4. A process as claimed in claim 1, wherein as monomers of group
   (a) acrylic acid, methacrylic acid or mixtures thereof in the form of the free acids or in a form partially or completely neutralized with alkali metal bases are used, and, as monomers of group
   (b) acrylic or methacrylic diesters of polyethylene glycols having a molecular weight of from 200 to 2,000 are used.

5. The process of claim 1, comprising 0.5–5 wt. % of said surfactant.

* * * * *